(12) United States Patent
Weber et al.

(10) Patent No.: US 6,380,172 B1
(45) Date of Patent: *Apr. 30, 2002

(54) MONOMERIC LIPOPHILIC OLIGOSACCHARIDE ANTIBIOTIC COMPOSITIONS

(75) Inventors: Patricia C. Weber, Yardley, PA (US); Ashit Kumar Ganguly, Upper Montclair, NJ (US); Paul Reichert, Montville, NJ (US); Charles W. McNemar, High Bridge, NJ (US); William T. Windsor, East Brunswick, NJ (US); Eric W. Kaler, Newark, DE (US)

(73) Assignee: Schering Corporation, Kenilworth, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/408,382

(22) Filed: Sep. 29, 1999

Related U.S. Application Data

(63) Continuation-in-part of application No. 08/708,513, filed on Sep. 5, 1996, which is a continuation-in-part of application No. 08/211,700, filed as application No. PCT/US92/08565 on Oct. 14, 1992, now Pat. No. 5,624,914, which is a continuation-in-part of application No. 07/777,864, filed on Oct. 16, 1991.

(51) Int. Cl.$^7$ .......... A61K 31/715; C08B 37/16
(52) U.S. Cl. .......... 514/54; 514/58
(58) Field of Search .......... 514/54, 58

(56) References Cited

U.S. PATENT DOCUMENTS

| | | | |
|---|---|---|---|
| 4,622,314 A | 11/1986 | Ganguly et al. | 514/54 |
| 4,767,748 A | 8/1988 | Ganguly et al. | 514/54 |
| 5,624,914 A | 4/1997 | Patel et al. | 514/54 |
| 5,776,912 A | 7/1998 | Patel et al. | 514/54 |
| 5,948,688 A | 9/1999 | Weber et al. | 436/71 |

FOREIGN PATENT DOCUMENTS

| | | | |
|---|---|---|---|
| WO | WO 98/28011 | 2/1998 | A61K/47/48 |

OTHER PUBLICATIONS

Szejtli, J., Cyclodextrins In Drug Formulations: Part II, Pharmaceutical Technology, Aug. 1991, pp. 24–38.

*Primary Examiner*—Gary Geist
*Assistant Examiner*—Everett White
(74) *Attorney, Agent, or Firm*—Peggy Albanese; Elliott Korsen

(57) ABSTRACT

This invention relates to pharmaceutical composition comprising a lipophilic oligosaccharide antibiotic in a substantially monomeric form.

11 Claims, No Drawings

MONOMERIC LIPOPHILIC OLIGOSACCHARIDE ANTIBIOTIC COMPOSITIONS

The present application is a continuation-in-part of pending U.S. Ser. No. 08/708,513 filed Sep. 5, 1996, which is in turn a continuation-in-part of pending U.S. application Ser. No. 08/211,700 filed Apr. 12, 1994, which is the United States national application corresponding to International Application No. PCT/US92/08565, filed Oct. 14, 1992 and designating the United States, now issued as U.S. Pat. No. 5,624,914, said PCT application is in turn a continuation-in-part of U.S. application Ser. No. 07/777,864, filed Oct. 16, 1991, the benefit of which applications are claimed pursuant to the provisions of 35 U.S.C. 120, 363 and 365(C).

FIELD OF THE INVENTION

This invention relates to a pharmaceutical composition comprising a lipophilic oligosaccharide antibiotic in a substantially monomeric form.

BACKGROUND OF THE INVENTION

Lipophilic oligosaccharide antibiotics such as the everninomicins, curamycins, avilamycins and flambamycins are members of the orthosomycin family of antibiotics which contain at least one acidic phenolic hydrogen, and two orthoester linkages associated with carbohydrate residues. See, A. K. Ganguly in "Kirk-Othmer, Encyclopedia of Chemical Technology" (1978), Volume 2, pp. 205–209, Third Edition, John Wiley and Sons and W. D. Ollis et al., *Tetrahedron* (1 979), Volume 35, pp. 105–127. These lipophilic oligosaccharide antibiotics exhibit broad spectrum biological activity against gram positive and gram negative bacteria in various in vitro assays, and in vivo activity in animal models such as mice. However, the injection of these lipophilic oligosaccharide antibiotics can cause an adverse reaction syndrome in mice. The symptoms of the adverse reaction syndrome include: incoordination, ataxia, lateral recumbency, urination, hind leg rigidity, labored breathing, and cardiac arrest.

The art has experimented with the use of cyclodextrins to enhance the solubility and bioavailability of drugs to avoid the adverse reaction syndrome. Cyclodextrins are modified starches made from glucopyranose units and include α-cyclodextrin consisting of six glucopyranose units, β-cyclodextrin consisting of seven glucopyranose units, and γ-cyclodextrin consisting of eight glucopyranose units. The α-, β- and γ-cyclodextrins and derivatives thereof have an inside surface or cavity which is lipophilic and an outer surface which is hydrophilic. This combination of a hydrophobic cavity and a hydrophilic outer surface has led to the use of cyclodextrins and derivatives thereof for the molecular complexation or encapsulation of many hydrophobic and/or unstable drugs of suitable dimensions, thereby improving solubility, stability and bioavailability of such drugs. Derivatives of α-, β-, and γ-cyclodextrins such as the hydroxypropyl-β-cyclodextrins, are disclosed by Jozsef Szejtli in *Pharmaceutical Technology*, June 1991, pp. 36–40. Complexes of α-, β-and γ-cyclodextrins, mixtures and derivatives thereof are disclosed in, U.S. Pat. No. 4,983,586 to Bodor. Specifically, U.S. Pat. No. 4,983,586 discloses a method of decreasing the incidence of precipitation of a lipophilic or water labile drug occurring at/or near the injection site and/or in the lungs following parenteral administration, by parenterally administering said drug in an aqueous solution containing a large quantity, i.e., 20 to about 50 weight percent of hydroxypropyl-β-cyclodextrin. U.S. Pat. No. 4,727,064 and *The International J. of Pharmaceutics*, (1986) 29, 73–82 disclose the use of a concentrated, i.e., 40–60 weight percent, aqueous solution of hydroxypropyl-β-cyclodextrin to solubilize various drugs such as acetaminophen, sex steroids, cardiac glycosides such as digoxin, as well as retinoic acid and acid salts thereof. See also, Pitha, U.S. Pat. No. 4,596,795 which discloses the administration of testosterone, progesterone and estradiol as complexes with poly-β-cyclodextrin or hydroxypropyl-β-cyclodextrin.

Janssen Pharmaceutica N.V. International Patent Application No. PCT/EP84/00417 published under International Publication No. WO 85/02767 on Jul. 4, 1985 discloses pharmaceutical compositions comprising complexes of drugs which are unstable or only sparingly soluble in water with partially etherified β-cyclodextrin ("β-CD") of the Formula (β-CD)-OR wherein the residue R is hydroxyethyl, hydroxypropyl, dihydroxypropyl and part of the residue R may optionally be alkyl groups, especially methyl or ethyl.

U.S. Pat. No. 5,624,914 teaches lipophilic oligosaccharide compositions, containing a lipophilic oligosaccharide antibiotic, NMG, cyclodextrins, a non-ionic surfactant, and optionally mannitol, sodium chloride, or glucose which are useful in avoiding the adverse reaction syndrome. Finally, U.S. Pat. No. 5,776,912 discloses oligosaccharide antibiotic compositions containing said oligosaccharide antibiotic, human serum albumin as a binding agent and optionally a tonicity agent such as mannitol. Said compositions avoid the adverse reaction syndrome. The human serum albumin is said to be a cheaper, generally recognized as safe (GRAS) alternative to cyclodextrins.

Surprisingly, Applicants have discovered an oligosaccharide antibiotic composition wherein said oligosaccharide antibiotic is in a substantially monomeric form. Said substantially monomeric form prevents the occurrence of the adverse reaction syndrome.

DEFINITIONS AND USAGES OF TERMS

The term "particles of monomeric form", as used herein, means that the oligosaccharide antibiotic is in particle form, and said particles have a hydrodynamic radius of about 5 to 50 Angstroms (Å). Specifically, said particles of monomeric form have a hydrodynamic radius of about 5 to 50 Å, preferably 7 to 40 Å; most preferably 10 to 30 Å.

The term "substantially monomeric", as used herein means that the particles of monomeric form contribute 35% to 100% of the total intensity of the linewidth distribution function. This means that about 80 to 100% of the drug by weight is present in particles of monomeric form. The remaining drug is present in other forms (dimer, trimer, multimer).

The term "tonicity agent", as used herein, means an agent which allows the pharmaceutical compositions of the present invention to have an osmolarity compatible with human serum. Typically, suitable tonicity agents, which may be present in the pharmaceutical compositions of the present invention, include mannitol, sodium chloride, glycine and dextrose. The preferred tonicity agent (when one is used) is mannitol but any pharmaceutically acceptable tonicity agent would also be acceptable.

The term "uniformity agent", as used herein, means a compound that increases the relative population of monomers in solution. Uniformity agents can be surfactants such as the nonionic, cationic, anionic, and amphoteric surfactants.

The terms "amphoteric" and "zwitterionic" are used interchangeably herein.

The terms "particles of monomeric form" and "monomeric form" are used interchangeably herein.

All percentages are weight percentages unless otherwise indicated.

SUMMARY OF THE INVENTION

The present invention relates to an aqueous pharmaceutical composition comprising an oligosaccharide antibiotic in substantially monomeric form.

DETAILED DESCRIPTION OF THE INVENTION

The present invention relates to an aqueous pharmaceutical composition comprising an oligosaccharide antibiotic in substantially monomeric form.

Specifically, Applicants' composition, wherein the antibiotic is blended with selected bases, tonicity agents, uniformity agents, and cyclodextrins, stabilizes the antibiotic in solution in a substantially monomeric form. In its substantially monomeric form 80–100% of the antibiotic is in monomeric form. The substantially monomeric form of the oligosaccharide antibiotic in the present invention maintains the antibiotic in soluble form. Specifically, the oligosaccharide antibiotic is maintained in particles of monomeric form having a hydrodynamic radius of 5–50 Å. Thus, the adverse reaction syndrome is avoided because the antibiotic does not aggregate and it stays in solution.

The "substantially monomeric" nature of the oligosaccharide of the present invention is experimentally measured using quasielastic light scattering technique. Quasielastic light scattering, is also known as photon correlation spectroscopy (PCS), as described in Madani and Kaler (Part. Part. Syst. Charact., Vol. 8, pp. 259–266, (1991)), Berne and Pecora ("Dynamic Light Scattering", John Wiley, New York, 1976) and/or D. H. Everett ("Basic Principles of Colloid Science", Royal Society of Chemistry, London, 1988). This can be accomplished using a variety of commercially available spectrometers such as (Brookhaven Model BI-200SM goniometer and Model BI-9000AT correlator) and a Lexel 300 mW Ar laser (488 nm wavelength). Specifically, samples are placed in 2 ml disposable glass analysis tubes and equilibrated for 10 min. in the instrument at 25° C. The analyses indicated that the aqueous pharmaceutical composition contained the lipophilic oligosaccharide antibiotic in a substantially monomeric form having a hydrodynamic radius (R) of about 5 to 50 Angstroms (Å) wherein $$R = kT/(6\tau\mu D)$$

where R is the hydrodynamic radius, k is Boltzman's constant, T is the absolute temperature, $\tau$ is pi, $\mu$ is solvent viscosity and D is the diffusion coefficient. By determining the size of a particular particle, it is possible to also determine something about the aggregative form of that material. For example, a lipophilic oligosaccharide can exist in a suspension in a multiplicity of different sizes equating to monomeric, dimeric and various multimeric forms. By determining the relative sizes of various particles, one can understand the full nature of the suspension and all the particulate forms of the drug. See, U.S. Pat. No. 5,948,688, incorporated by reference herein. The contribution of a particular particle to the total intensity of the linewidth distribution function, G(Γ) can be used to evaluate the relative proportion of a particular sized particle. In addition, the substantially monomeric form contributed 35%–100% of the total intensity of the linewidth distribution function, G(Γ) wherein $$G(\Gamma) = M^2(r)P(q)S(q) \tag{3}$$

where G(Γ) is the linewidth distribution function, M(r) is the mass distribution of the particles of size r, P(q) is the particle form factor and S(q) is the static structure factor. G (Γ) is derived from quasielastic light scattering procedures which measure the intensity autocorrelation function, $g^{(2)}$ (τ) wherein $$g^{(2)}(\tau) = A(1+\beta|g^{(1)}(\tau)|^2) \tag{2}$$

where $g^{(2)}$ (τ) is the intensity autocorrelation function, A is the background scattered intensity, τ is the signal-to-noise ratio, and $g^{(1)}$ (τ) is the electric field autocorrelation function. The measured intensity autocorrelation function, $g^{(2)}$ (τ) is related to the linewidth distribution function, G (Γ) by the following formula:

$$g^{(1)}(\tau) = \int_0^\infty G(\Gamma)\exp(-\Gamma\tau)d\Gamma \tag{1}$$

where $g^{(1)}$ (τ) is the electric field autocorrelation function. The decay constant, Γ equals $Dq^2$ where D is the diffusion coefficient and q is the magnitude of the scattering vector where q=(4πn/λ) sin (Θ/2) where π is pi, n is the refractive index of the medium, λ is the wavelength of light in the scattering medium and Θ is the scattering angle.

The analysis of solutions by photon correlation spectroscopy can therefore provide information about the hydrodynamic radius, and distribution of particles in solution. If the same procedure is repeated with a different drug content, a suspending liquid including the same components in different proportions, or a different suspending formulation, then the effects thereof on the physical characteristics of the lipophilic oligosaccharide antibiotic and/or suspension can be determined. This is accomplished by comparing the results of the two formulations in terms of the presence or absence of certain sized particles as well as changes in the relative proportion of the particles.

Thus, in the present invention, the particles of monomeric form of the oligosaccharide antibiotic, in an aqueous composition, have a hydrodynamic radius of about 5 to 50 Angstroms (Å); preferably 7 to 40 Å; most preferably 10 to 30 Å. Preferably, said particles of monomeric form contribute 35–100% of the total intensity of the linewidth distribution function. More preferably, said particles of monomeric form contribute 45–100%, and most preferably said particles of monomeric form contribute 55–100% of the linewidth distribution function. This means that about 80 to about 100% of the drug by weight is present in particles of monomeric form, preferably 85–100% of the drug by weight is present in particles of monomeric form, and more preferably 90–99% of the drug by weight is present in particles of monomeric form. In other words, the drug is substantially monomeric. The remaining drug is present in other forms (dimer, trimer, multimer).

Preparing the Substantially Monomeric Oligosaccharide Antibiotic Compositions of the Present Invention Oligosaccharide Antibiotics Useful in the Practice of the Present Invention The oligosaccharide antibiotics useful in the practice of the present invention are selected from the group including, but not limited to, everninomicin, avilamycin, curamycin and flambamycin. Further, oligosaccharide antibiotics useful in the practice of the present invention are described in U.S. Pat. Nos. 4,597,968; 5,624,914; 4,622,314; 5,763,600; 5,776,912 and 4,767,748, all incorporated by reference herein. The preferred oligosaccharide antibiotics are everninomicin; curamycin and avilamycin. The most preferred is everninomicin whose chemical name is 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate).

The oligosaccharide antibiotics are present in the compositions at levels of 0.1 to 10% by weight; more preferably 0.2 to 8% by weight, and most preferably 0.5 to 6% by weight.

Solubilizing Agents Useful in the Practice of the Present Invention

The solubilizing agents useful in the present invention are selected from the group consisting of hydroxylpropyl α-, β- and γ-cyclodextrins. Suitable cyclodextrins are disclosed in U.S. Pat. No. 5,624,914 incorporated by reference herein. The preferred solubilizing agent is hydroxyl propyl-β-cyclodextrin.

The solubilizing agents are present in the compositions at levels of 1 to 60% by weight; more preferably 2 to 40% by weight and most preferably 3 to 30% by weight.

Solubilizing Bases Useful in the Practice of the Present Invention

Inorganic and organic bases are useful in the practice of the present invention as solubilizing bases. Said solubilizing bases include, but are not limited to, N-methylglucamine (NMG), diethanolamine, tris-aminomethane, glycine-sodium hydroxide, and sodium bicarbonate. Suitable solubilizing bases are also disclosed in U.S. Pat. No. 5,624,914 incorporated by reference herein. The preferred solubilizing bases are NMG, glycine-sodium hydroxide, sodium bicarbonate. The most preferred solubilizing base is NMG.

The solubilizing base is present in the composition of the present invention at levels of 0.1 to 10% by weight; more preferably 0.3 to 8% by weight and most preferably 0.2 to 5.0% by weight.

Surfactants Useful in the Practice of the Present Invention

The surfactants act as uniformity agents by increasing the relative population of oligosaccharide antibiotic monomers in solution. A large number of surfactants with various combinations of hydrophobic and hydrophilic groups are commercially available for use in the present invention. Preferably, the surfactants are suitable for pharmaceutical use. Specifically, surfactants useful in the practice of the present invention are nonionic, cationic, anionic and amphoteric (also known as zwitterionic) and mixtures thereof.

Nonionic Surfactants

Nonionic surfactants include, but are not limited to:

(a) polyoxyethylene or polyoxypropylene condensates of aliphatic carboxylic acids, whether linear or branched-chain and unsaturated or saturated, containing from about 8 to about 18 carbon atoms in the aliphatic chain and incorporating from 5 to about 50 ethylene oxide or propylene oxide units. Suitable carboxylic acids include "coconut" fatty acids (derived from coconut oil) which contain an average of about 12 carbon atoms, "tallow" fatty acids (derived from tallow-class fats) which contain an average of about 18 carbon atoms, palmitic acid, myristic acid, stearic acid and lauric acid.

b) polyoxyalkylene (polyoxyethylene or polyoxypropylene) condensates of aliphatic alcohols, whether linear- or branched- chain and unsaturated or saturated, containing from about 8 to about 24 carbon atoms and incorporating from about 5 to about 50 ethylene oxide or propylene oxide units. Suitable alcohols include the "coconut" fatty alcohol, "tallow" fatty alcohol, lauryl alcohol, myristyl alcohol and oleyl alcohol. INDUSTROL® DW5 is a representative condensate of an aliphatic alcohol type surfactant. INDUSTROL® DW5 is available from BASF Corporation, Mt. Olive, N.J.

(c) polyoxyalkylene (polyoxyethylene or polyoxypropylene) condensates of alkyl phenols, whether linear- or branched- chain and unsaturated or saturated, containing from about 6 to about 12 carbon atoms and incorporating from about 5 to about 25 moles of ethylene oxide or propylene oxide.

(d) Polyalkylene oxide block copolymers. This class includes polyethoxylated polypropoxylated propylene glycol sold under the tradename "PLURONIC®" made by the BASF Corporation or polypropoxylated-polyethoxylated ethylene glycol sold under the tradename "PLURONIC®" available from BASF Corporation, Mt. Olive, N.J. The first group of compounds are formed by condensing ethylene oxide with a hydrophobic base formed by the condensation of propylene oxide with propylene glycol. The hydrophobic portion of the molecule which, of course, exhibits water insolubility, has a molecular weight from about 1500 to 1800. The addition of the polyoxyethylene radicals to this hydrophobic portion tends to increase the water solubility of the molecule as a whole and the liquid character of the product is retained up to the point where the polyoxyethylene content is about 50% of the total weight of the condensation product. The latter series of compounds called "PLURONIC®" are formed by condensing propylene oxide with the polyethoxylated ethylene glycol condensate. This series of compounds is characterized by having an average molecular weight of about between 2000 and 9000 consisting of, by weight, from about 10 to 80% polyoxyethylene, and a polyoxypropylene portion having a molecular weight between about 1000 and 3100.

Other useful non-ionic surfactants are the primary aliphatic alcohol ethoxylates, secondary aliphatic alcohol ethoxylates, alkylphenol ethoxylates and ethylene-oxide-propylene oxide condensates of primary alkanols, such as the PLURAFAC® series available from BASF and the condensates of ethylene oxide with sorbitan fatty acid esters such as the TWEEN® series available from ICI. The PLURAFAC® series are the condensation products of an organic aliphatic or alkyl aromatic hydrophobic compound and hydrophilic ethylene oxide groups. Practically any hydrophobic compound having a carboxy, hydroxy, amido, or amino group with a free hydrogen attached to the nitrogen can be condensed with ethylene oxide or with the polyhydration product thereof, polyethylene glycol, to form these water-soluble nonionic surfactants. Further, the length of the polyethylene chain can be adjusted to achieve the desired balance between the hydrophobic and hydrophilic elements.

The TWEEN® series are condensates of 2 to 30 moles of ethylene oxide with sorbitan mono- and tri-$C_{10}$–$C_{20}$ alkanoic acid esters having a hydrophilic/lipophilic balance (HLB) of 8 to 15 also may be used in the present invention. The HLB is a numeric rating system for the combined hydrophilic and lipophilic characteristics of an amphiphilic molecule that contains both hydrophilic and lipophilic moieties, and thus is a measure of the emulsifying efficiency of a surfactant. The HLB is related to the polarity of the molecule, the least hydrophilic surfactants having low HLB numbers, and increasing numbers corresponding to increasing hydrophilic character. For example, a non-ionic surfactant having a low HLB value (i.e., less than about 10) is considered soluble in hydrophobic substances and favors water-in-hydrophobic substance emulsions, while a surfactant having a high HLB value (i.e., greater than about 13) is associated with a water-soluble surfactant and favors hydrophobic substance-in-water emulsions.

The nonionic surfactant class also includes the condensation products of a higher alcohol (e.g., an alkanol containing about 8 to 18 carbon atoms in a straight or branched chain configuration) condensed with about 5 to 30 moles of ethylene oxide, for example, lauryl or myristyl alcohol condensed with about 16 moles of ethylene oxide (EO), tridecanol condensed with about 6 to 11 moles of EO, myristyl alcohol condensed with about 10 moles of EO per mole of myristyl alcohol, the condensation product of EO with a cut of coconut fatty alcohol containing a mixture of fatty alcohols with alkyl chains varying from 10 to about 14 carbon atoms in length and wherein the condensate contains either about 6 moles of EO per mole of total alcohol or about 9 moles of EO per mole of alcohol and tallow alcohol ethoxylates containing 6 to 11 EO per mole of alcohol.

The NEODOL® ethoxylate series (Shell Co.) are also useful. They are higher aliphatic, primary alcohols containing about 9–15 carbon atoms, such as $C_{11}$ alkanol condensed with 9 moles of ethylene oxide (NEODOL® 1-9), $C_{12-13}$ alkanol condensed with 6.5 moles ethylene oxide (NEODOL® 23-6.5), $C_{12-15}$ alkanol condensed with 7 or 3 moles ethylene oxide (NEODOL® 25-7 or NEODOL® 25-3), and $C_{14-15}$ alkanol condensed with 13 moles ethylene oxide (NEODOL® 45-13). Such ethoxamers have an HLB value of about 8 to 15 and give good oil/water emulsification, whereas ethoxamers with HLB values below 8 contain less than 5 ethyleneoxide groups and tend to be poor emulsifiers and poor detergents.

Additional satisfactory water soluble alcohol ethylene oxide condensates are the condensation products of a secondary aliphatic alcohol containing 8 to 18 carbon atoms in a straight or branched chain configuration condensed with 5 to 30 moles of ethylene oxide. Examples of commercially available nonionic detergents of the foregoing type are $C_{11}$–$C_{15}$ secondary alkanol condensed with either 9 EO (TERGITOL® 15-S-9) or 12 EO (TERGITOL® 15-S-12) marketed by Union Carbide.

Other suitable nonionic detergents include the polyethylene oxide condensates of one mole of alkyl phenol containing from about 8 to 18 carbon atoms in a straight- or branched chain alkyl group with about 5 to 30 moles of ethylene oxide. Specific examples of alkyl phenol ethoxylates include nonyl condensed with about 9.5 moles of EO per mole of nonyl phenol, dinonyl phenol condensed with about 12 moles of EO per mole of phenol, dinonyl phenol condensed with about 15 moles of EO per mole of phenol and di-isoctylphenol condensed with about 15 moles of EO per mole of phenol. Commercially available nonionic surfactants of this type include IGEPAL® CO-630 (nonyl phenol ethoxylate) marketed by GAF Corporation.

Finally, Surfactant Science Series, edited by Martin J. Schick, Nonlonic Surfactants, Vols. 19 and 23 provide detailed descriptions of useful nonionic surfactants.

Preferred non-ionic surfactants useful in the practice of the present invention are selected from the group consisting of polysorbate 80 (TWEEN® 80), polysorbate 20 (TWEEN® 20), and polyoxyalkylene oxides such as polyoxyethylene lauryl ether (BRIJ® 35). The most preferred non-ionic surfactant is TWEEN® 80.

The non-ionic surfactant is present in the composition of the present invention at levels of 0.001 to 6%; more preferably 0.005 to 5% and most preferably 0.01 to 2.5% by weight on the basis of the 56-deacetyl-57-demethyls-45-O-de(2-methyl-1-oxopropyl)-12-O-(2,3,6-trideoxy-3-C-methyl-4-O-methyl-3-nitro-α-L-arabino -hexopyransoyl)-flambamycin 56-(2,4-dihydroxy-6-methylbenzoate).

Anionic Surfactants

Useful anionic surfactants include, but are not limited to, the water-soluble salts, preferably the alkali metal, ammonium and substituted ammonium salts, of organic sulfuric acid reaction products having in their molecular structure of alkyl group containing from about 10 to about 20 carbon atoms and a sulfonic acid or sulfuric acid ester group. (Included in the term "alkyl" is the alkyl portion of acyl groups.) Examples of this group of synthetic surfactants are the sodium and potassium alkyl sulfates, especially those obtained by sulfating the higher alcohols ($C_8$–$C_{18}$ carbon atoms) such as those produced by reducing the glycerides of tallow or coconut oil; and the sodium and potassium alkylbenzenesulfonates in which the alkyl group contains from about 9 to about 15 carbon atoms in straight chain or branched chain configuration, e.g., those of the type described in U.S. Pat. Nos. 2,220,099 and 2,477,383 both of which are incorporated herein by reference.

Other anionic surfactants suitable for use herein are the sodium alkyl glyceryl ether sulfonates, especially those ethers of higher alcohols derived from tallow and coconut oil; sodium coconut oil fatty acid monoglyceride sulfonates and sulfates; sodium or potassium salts of alkyl phenol ethylene oxide ether sulfates containing from about 1 to about 10 units of ethylene oxide per molecule and from about 8 to about 12 carbon atoms in the alkyl group; and sodium or potassium salts of alkyl ethylene oxide ether sulfates containing from about 1 to about 25 units of ethylene oxide per molecule and from about 10 to about 20 carbon atoms in the alkyl group. Also useful in the practice of the present invention are water-soluble salts including the sodium, potassium, ammonium and ethanolammonium salts of linear $C_8$–$C_{16}$ alkyl benzene sulfonates; $C_{10}$–$C_{20}$ paraffin sulfonates, alpha olefin sulfonates containing about 10–24 carbon atoms and $C_8$–$C_{18}$ alkyl sulfates and mixtures thereof.

The paraffin sulfonates may be monosulfonates or di-sulfonates and usually are mixtures thereof, obtained by sulfonating paraffins of 10 to 20 carbon atoms. Preferred paraffin sulfonates are those of $C_{12-18}$ carbon atoms chains, and more preferably they are of $C_{14-17}$ chains. Paraffin sulfonates that have the sulfonate group(s) distributed along the paraffin chain are described in U.S. Pat. Nos. 2,503,280; 2,507,088; 3,260,744; and 3,372,188; and also in German Patent 735,096. Such compounds may be made to specifications and desirably the content of paraffin sulfonates outside the $C_{14-17}$ range will be minor and will be minimized, as will be any contents of di- or poly-sulfonates.

Other examples of suitable sulfonated anionic detergents are the well known higher alkyl mononuclear aromatic sulfonates, such as the higher alkylbenzene sulfonates containing 9 to 18 or preferably 9 to 16 carbon atoms in the higher alkyl group in a straight or branched chain, or $C_{8-15}$ alkyl toluene sulfonates.

Other useful anionic surfactants include the water-soluble salts of esters of alpha-sulfonated fatty acids containing from about 6 to 20 carbon atoms in the fatty acid group and from about 1 to 10 carbon atoms in the ester group; water-soluble salts of 2-acyloxy-alkane-1-sulfonic acids containing from about 9 to about 23 carbon atoms in the alkyl group and from about 8 to 20 carbon atoms in the moiety.

Preferred anionic surfactants useful in the practice of the present invention are selected from the group consisting of negatively charged sulfate groups such as sodium dodecyl sulfate (SDS) and Sulfobutanedioc acid bis[2-ethyl-hexyl ester]dioctyl sulfosuccinate (Docusate sodium). Also, bile acid salts (sodium salts of cholic acid and deoxycholic acid) containing a rigid hydrophobic group structurally similar to steroids. The most preferred anionic surfactant is sodium dodecyl sulfate (SDS).

The anionic surfactant is present in the composition of the present invention at levels of 0.001 to 6%; more preferably 0.005 to 5% and most preferably 0.01 to 2.5% by weight on the basis of the 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate).

Cationic Surfactants

Cationic surfactants, useful in the practice of the present invention, comprise a wide variety of compounds characterized by one or more organic hydrophobic groups and generally by a quaternary nitrogen associated with the acid radical. Quaternary nitrogen compounds also include nitrogen-containing ring compounds. Suitable anions are halides, methyl sulfate and hydroxide. A more complete disclosure of cationic surfactants can be found in U.S. Pat. No. 4,228,044, issued Oct. 14, 1980, to Cambre, said patent being incorporated herein by reference. Cationic surfactants of the quaternary ammonium salt variety include but are not limited to:

1. cetyl trimethylammonium bromide;
2. benzyl dimethylmyristylammonium chloride;
3. benzyl methylethylcetylammonium chloride;
4. stearyl trimethylammonium chloride;
5. myristyl dimethylethylammonium chloride.

Additional cationic surfactants useful in the practice of the present invention are copolymers of vinyl monomers having cationic protonated amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone. The alkyl and dialkyl substituted monomers preferably have from $C_1$ to $C_7$ alkyl groups, more preferably from $C_1$ to $C_3$ alkyl groups. Other suitable spacer monomers include vinyl esters, vinyl alcohol (made by hydrolysis of polyvinyl acetate), maleic anhydride, propylene glycol, and ethylene glycol.

Suitable cationic protonated amino and quaternary ammonium monomers include vinyl compounds substituted with dialkylaminoalkyl acrylate, dialkylaminoalkyl methacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the $C_1$, $C_2$ or $C_3$ alkyls.

Suitable amine-substituted vinyl monomers include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$ alkyls.

Other suitable cationic polymers include copolymers of 1-vinyl-2-pyrrolidone and 1-vinyl-3-methylimidazolium salt (e.g., chloride salt) (referred to in the industry by the Cosmetic, Toiletry, and Fragrance Association, "CTFA", as Polyquaternium-16), such as those commercially available from BASF Corp. (Mt. Olive, N.J., U.S.A.) under the LUVIQUAT® trade name (e.g., LUVIQUAT® FC 370); copolymers of 1-vinyl-2-pyrrolidone and dimethylaminoethyl methacrylate (referred to in the industry by CTFA as Polyquaternium-11) such as those commercially available from ISP Corporation (Wayne, N.J., U.S.A.) under the GAFQUAT® trade name (e.g., GAFQUAT® 755N); cationic diallyl quaternary ammonium-containing polymers, including, for example, dimethyldiallylammonium chloride homopolymer and copolymers of acrylamide and dimethyl-diallylammonium chloride, referred to in the industry (CTFA) as Polyquaternium 6 and Polyquaternium 7, respectively; and mineral acid salts of amino-alkyl esters of homopolymers and copolymers of unsaturated carboxylic acids having from 3 to 5 carbon atoms, as described in U.S. Pat. No. 4,009,256, which description is incorporated herein by reference.

Other suitable cationic polymers include polysaccharide polymers, such as cationic cellulose derivatives and cationic starch derivatives. Suitable cationic polysaccharide polymers include those which conform to the formula

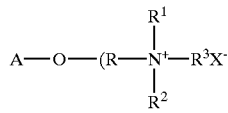

wherein A is an anhydroglucose residual group, such as a starch or cellulose anhydroglucose residual; R is an alkylene oxyalkylene, polyoxyalkylene, or hydroxyalkylene group, or combination thereof, $R^1$, $R^2$, and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less; and X is an anionic counterion.

Useful cationic cellulose polymers are available from Amerchol Corp. (Edison, N.J., USA) in their Polymer JR and LR series of polymers, as salts of hydroxyethyl cellulose reacted with trimethyl ammonium substituted epoxide, referred to as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the trade name POLYMER® LM-200.

Other suitable cationic polymers include cationic guar gum derivatives, such as guar hydroxypropyltrimonium chloride, specific examples of which include the JAGUAR® series commercially available from Rhodia. Other suitable cationic polymers include quaternary nitrogen-containing cellulose ethers, some examples of which are described in U.S. Pat. No. 3,962,418, which description is incorporated herein by reference herein. Other suitable cationic polymers include copolymers of etherified cellulose, guar and starch, some examples of which are described in U.S. Pat. No. 3,958,581, which description is incorporated herein by reference.

Preferred cationic surfactants useful in the practice of the present invention are selected from the group consisting of positively charged alkyl ammonium groups such as cetyl trimethylammonium bromide (CTAB). The most preferred cationic surfactant is cetyl trimethylammonium bromide (CTAB).

The cationic surfactant is present in the composition of the present invention at levels of 0.001 to 6%; more preferably 0.005 to 5% and most preferably 0.01 to 2.5% by weight on the basis of the 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate).

Amphoteric Surfactants

The term "amphoteric surfactant," as used herein, is also intended to encompass "zwitterionic surfactants", which are well known to those skilled in the art as a subset of amphoteric surfactants. Amphoteric surfactants offer the combined properties of ionic and non-ionic surfactants. Like non-ionic surfactants the amphoteric surfactants do not possess a net charge. Amphoteric surfactants include, but are not limited to, 3-[(3cholamidopropyl)dimethylammonio]-1-propanesulfonate (CHAPS), 3-[(3cholamidopropyl)dimethylammonio]-2-hydroxy-1-propanesulfonate (CHAPSO), and N,N-bis[3-D-gluconamidopropyl]-cholamide (BIGCHAP).

Additional nonlimiting examples of amphoteric or zwitterionic surfactants are those selected from the group consisting of betaines, sultaines, hydroxysultaines, alkyliminoacetates, iminodialkanoates, aminoalkanoates, and mixtures thereof.

Examples of betaines include the higher alkyl betaines, such as coco dimethyl carboxymethyl betaine, lauryl dimethyl carboxymethyl betaine, lauryl dimethyl alpha-carboxyethyl betaine, cetyl dimethyl carboxymethyl betaine, cetyl dimethyl betaine (available as LONZAINE® 16SP from Lonza Corp.), lauryl bis-(2-hydroxyethyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, lauryl dimethyl sulfoethyl betaine, lauryl bis-(2-hydroxyethyl)sulfopropyl betaine, amidobetaines and amidosulfobetaines (wherein the RCONH(CH$_2$)$_3$ radical is attached to the nitrogen atom of the betaine), oleyl betaine (available as amphoteric VELVETEX® OLB-50 from Henkel), and cocamidopropyl betaine (available as VELVETEX® BK-35 and BA-35 from Henkel).

Examples of sultaines and hydroxysultaines include materials such as cocamidopropyl hydroxysultaine (available as MIRATAINE® CBS from Rhone-Poulenc).

Suitable for use herein are amphoteric surfactants having the following structure:

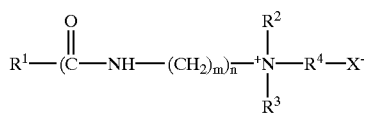

wherein $R^1$ is an unsubstituted, saturated or unsaturated, straight or branched chain alkyl having from about 9 to about 22 carbon atoms. Preferred $R^1$ has from about 11 to about 18 carbon atoms; more preferably from about 12 to about 18 carbon atoms; more preferably still from about 14 to about 18 carbon atoms; m is an integer from 1 to about 3, more preferably from about 2 to about 3, and more preferably about 3; n is either 0 or 1, preferably 1; $R^2$ and $R^3$ are independently selected from the group consisting of alkyl having from 1 to about 3 carbon atoms, unsubstituted or mono-substituted with hydroxy, preferred $R^2$ and $R^3$ are $CH^3$; X is selected from the group consisting of $CO_2$, $SO_3$ and $SO_4$, $R^4$ is selected from the group consisting of saturated or unsaturated, straight or branched chain alkyl, unsubstituted or monosubstituted with hydroxy, having from 1 to about 5 carbon atoms. When X is $CO_2$, $R^4$ preferably has 1 or 3 carbon atoms, more preferably 1 carbon atom. When X is $SO_3$ or $SO_4$, $R^4$ preferably has from about 2 to about 4 carbon atoms, more preferably 3 carbon atoms.

Further examples of amphoteric surfactants useful in the practice of the present invention include:

Cetyl dimethyl betaine (this material also has the CTFA designation cetyl betaine)

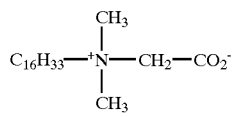

Cocamidopropylbetaine

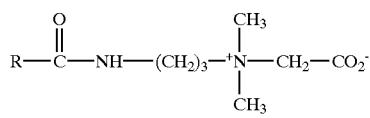

wherein R has from about 9 to about 13 carbon atoms.
Cocamidopropyl hydroxy sultaine

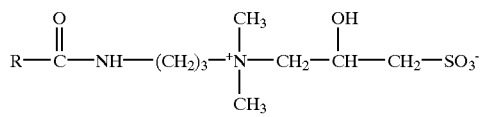

wherein R has from about 9 to about 13 carbon atoms.

Examples of other useful amphoteric surfactants are alkyliminoacetates, and iminodialkanoates and aminoalkanoates of the formulas RN[(CH$_2$)$_m$CO$_2$M]$_2$ and RNH(CH$_2$)$_m$CO$_2$M wherein m is from 1 to 4, R is a C$_8$–C$_{22}$ alkyl or alkenyl, and M is H, alkali metal, alkaline earth metal ammonium, or alkanolammonium. Also included are imidazolinium and ammonium derivatives. Specific examples of suitable amphoteric surfactants include sodium 3-dodecyl-aminopropionate, sodium 3-dodecylaminopropane sulfonate, N-higher alkyl aspartic acids such as those produced according to the teaching of U.S. Pat. No. 2,438,091 which is incorporated herein by reference in its entirety; and the products sold under the trade name MIRANOL® and described in U.S. Pat. No. 2,528,378, which is incorporated herein by reference in its entirety. Other examples of useful amphoterics include amphoteric phosphates, such as coamidopropyl PG-dimonium chloride phosphate (commercially available as MONAQUAT® PTC, from Mona Corp.). Also useful are amphoacetates such as disodium lauroamphodiacetate, sodium lauroamphoacetate, and mixtures thereof.

Further, nonlimiting examples of amphoteric surfactants useful in the compositions of the present invention are disclosed in McCutcheon's, *Detergents and Emulsifiers*, North American edition (1986), published by Allured Publishing Corporation; and McCutcheon's, *Functional Materials*, North American Edition (1992).

Preferred amphoteric surfactants useful in the practice of the present invention are selected from the group consisting of CHAPS, CHAPSO and BIGCHAP. The most preferred zwitterionic surfactant is BIGCHAP.

The zwitterionic surfactant is present in the composition of the present invention at levels of 0.001 to 6%; more preferably 0.005 to 5% and most preferably 0.01 to 2.5% by weight on the basis of the 56-deacetyl-57-demethyl-45-O- de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate).

Tonicity Agents Useful in the Practice of the Present Invention

Tonicity agents may be used in the practice of the present invention. The tonicity agents useful in the practice of the present invention may be selected from the group including, but not limited to, mannitol, sorbitol, xylitol, glycerol, sodium chloride, dextrose, sucrose and lactose. The preferred tonicity agent is mannitol.

The tonicity agents may be present in the compositions of the present invention at levels of 0.3 to 18% by weight; more preferably 0.6 to 15% by weight and most preferably 1.0 to 10% by weight.

Optional Ingredients Useful in the Practice of the Present Invention

Optional ingredients useful in preparing the compositions of the present invention include, but are not limited to: bacteriostatic agents, bulking agents, stabilizers and anti-oxidants.

The compositions are prepared by blending methods known to those skilled in the art. See, Remingtons, *Pharmaceutical Sciences*, 18$^{th}$ Edition.

EXAMPLES ILLUSTRATING THE PRESENT INVENTION

The following non-limiting Examples illustrate the compositions of the present invention.

Example 1

An aqueous solution containing 18.9 mg of N-methyl glucamine (NMG) and 262.5 mg of hydroxyl propyl-β-cyclodextrin (HPβCD) having 7.4 hydroxypropyl groups per molecule was prepared in 3 ml water. To this solution was added 52.5 mg of 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate). After mild agitation, a homogeneous complex containing 20 mg/ml of 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate) was formed. The molar ratios of the three components in the homogeneous solution so-formed were 1 mole of 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate) to 3 moles of NMG to 5 moles of HPβCD. To this solution was added 75 mg of granular mannitol, USP Grade and 1.5 mg of Polysorbate-80 (TWEEN®-80) NF. The weight percent of TWEEN®-80 is 2.85% of the basis of the 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate). The so-formed solution was filtered through a 0.45 μm membrane and analyzed by a quasielastic light scattering method as described herein.

Example 2

300 mg of hydroxyl propyl-β-cyclodextrin (HPβCD) having 7.4 hydroxypropyl groups per molecule and 60 mg of the compound 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate) were added to a 3 ml (total) aqueous solution of a 93 mM, pH 9.7 glycine-sodium hydroxide buffer (Gomori, Meth. Enzymol. 1,145 (1955)). The molar ratios of the three components in the homogeneous solution so-formed were 1 mole of 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate) to 7.4 moles of glycine-sodium hydroxide to 5 moles of HPβCD. To this solution was added 86 mg of granular mannitol, USP Grade and 1.7 mg of Polysorbate-80 (TWEEN®-80) NF. The weight percent of TWEEN®-80 is 2.85% of the basis of the 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate). The so-formed solution was filtered through a 0.45 μm membrane and analyzed by a quasielastic light scattering method as described herein.

Example 3

300 mg of hydroxyl propyl-β-cyclodextrin (HPβCD) having 7.4 hydroxypropyl groups per molecule and 60 mg of 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate) were added to a 3 ml (total) aqueous solution of a 83 mM, pH 9.7 sodium carbonate-sodium bicarbonate buffer (Delory and King, BJ 39,245 (1945)) prepared with USP grade water. The molar ratios of the three components in the homogeneous solution so-formed were 1 mole of 56-deacetyl-57-demethyl-45-O-de(2-methyl-1-oxopropyl)-12-O-(2,3,6-trideoxy-3-C-methyl-4-O-methyl-3-nitro-a-L-arabino-hexopyransoyl)-flambamycin 56-(2,4-dihydroxy-6-methylbenzoate) to 6.6 moles of sodium bicarbonate to moles of HPβCD. To this solution was added 86 mg of granular mannitol, USP Grade and 1.7 mg of Polysorbate-80 (TWEEN®-80) NF. The weight percent of TWEEN®-80 is 2.85% of the basis of the 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate). The so-formed solution was filtered through a 0.45 μm membrane and analyzed by a quasielastic light scattering method as described herein.

Example 4

An aqueous solution containing 21 mg of N-methyl glucamine (NMG) and 300 mg of hydroxyl propyl-β-cyclodextrin (HPβCD) having 7.4 hydroxypropyl groups per molecule was prepared in 3 ml water. To this solution was added 60 mg of 56-deacetyl-57-demethyl-45-O-de(2-methyl-1-oxopropyl)-12-O-(2,3,6-trideoxy-3 -C-methyl-4-O-methyl-3-nitro-α-L-arabino-hexopyransoyl)-flambamycin 56-(2,4-dihydroxy-6-methylbenzoate). After mild agitation, a homogeneous complex containing 20 mg/ml of 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate) was formed. The molar ratios of the three components in the homogeneous solution so-formed were 1 mole of 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate) to 3 moles of NMG to 5 moles of HPβCD. To this solution was added 86 mg of granular mannitol, USP Grade and 1.7 mg of polyoxyethylene lauryl ether (BRIJ® 35). The weight percent of BRIJ® 35 is 2.85% of the basis of 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate). The so-formed solution was filtered through a 0.45 μm membrane and analyzed by a quasielastic light scattering method as described herein.

Example 5

An aqueous solution containing 21 mg of N-methyl glucamine (NMG) and 300 mg of hydroxyl propyl-β-cyclodextrin (HPβCD) having 7.4 hydroxypropyl groups per molecule was prepared in 3 ml water. To this solution was added 60 mg of 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate). After mild agitation, a homogeneous complex containing 20 mg/ml of 56-deacetyl-57-demethyl-45-O-de(2-methyl-1-oxopropyl)-12 -O-(2,3,6-trideoxy-3-C-methyl-4-O-methyl-3-nitro-α-L-arabino-hexopyransoyl)-flambamycin 56-(2,4-dihydroxy-6-methylbenzoate) was formed. The molar ratios of the three components in the homogeneous solution so-formed where 1 mole of 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate) to 3 moles of NMG to 5 moles of HPβCD. To this solution was added 86 mg of granular mannitol, USP Grade and 1.7 mg sodium dodecyl sulfate (SDS). The weight percent of SDS is 2.85% of the basis of the 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate). The so-formed solution was filtered through a 0.45 μm membrane and analyzed by a quasielastic light scattering method as described herein.

Example 6

An aqueous solution containing 21 mg of N-methyl glucamine (NMG) and 300 mg of hydroxyl propyl-β-cyclodextrin (HPβCD) having 7.4 hydroxypropyl groups per molecule was prepared in 3 ml water. To this solution was added 60 mg of 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate). After mild agitation, a homogeneous complex containing 20 mg/ml of 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate) was formed. The molar ratios of the three components in the homogeneous solution so-formed were 1 mole of 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate) to 3 moles of NMG to 5 moles of HPβCD. To this solution was added 86 mg of granular mannitol, USP Grade and 1.7 mg of cetyl trimethyl-ammonium bromide (CTAB). The weight percent of CTAB is 2.85% of the basis of the 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate). The so-formed solution was filtered through a 0.45 μm membrane and analyzed by a quasielastic light scattering method as described herein.

Example 7

An aqueous solution containing 21 mg of N-methyl glucamine (NMG) and 300 mg of hydroxyl propyl-β-cyclodextrin (HPβCD) having 7.4 hydroxypropyl groups per molecule was prepared in 3 ml water. To this solution was added 60 mg of 56-deacetyl-57-demethyl-45-O-de(2-methyl-l1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate). After mild agitation, a homogeneous complex containing 20 mg/ml of 56-deacetyl-57-demethyl-45-O-de(2-methyl-1-oxopropyl)-12-flambamycin 56-(2,4-dihydroxy-6-methylbenzoate) was formed. The molar ratios of the three components in the homogeneous solution so-formed were 1 mole of 56-deacetyl-57-demethyl-45-O-de(2-methyl-1-oxopropyl)-12-O-(2,3,6-trideoxy-3-C-methyl- 4-O-methyl-3-nitro-α-L-arabino-hexopyransoyl)-flambamycin 56-(2,4-dihydroxy-6-methylbenzoate) to 3 moles of NMG to 5 moles of HPβCD. To this solution was added 86 mg of granular mannitol, USP Grade and 1.7 mg of N, N-bis[3-D-gluconamidopropyl]-cholamide (BIGCHAP). The weight percent of BIGCHAP is 2.85% of the basis of the 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate). The so-formed solution was filtered through a 0.45 μm membrane and analyzed by a quasielastic light scattering method as described herein.

Example 8

An aqueous solution containing 21 mg of N-methyl glucamine (NMG) and 300 mg of hydroxyl propyl-β-cyclodextrin (HPβCD) having 7.4 hydroxypropyl groups per molecule was prepared in 3 ml water. To this solution was added 60 mg of 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate). After mild agitation, a homogeneous complex containing 20 mg/ml of 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate) was formed. The molar ratios of the three components in the homogeneous solution so-formed were 1 mole of 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate) to 3 moles of NMG to 5 moles of HPβCD. To this solution was added 86 mg of granular lactose, USP Grade and 1.7 mg of Polysorbate-80 (TWEEN®-80) NF. The weight percent of TWEEN®-80 is 2.85% of the basis of the 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate). The so-formed solution was filtered through a 0.45 μm membrane and analyzed by a quasielastic light scattering method as described herein.

Quasielastic Light Scattering Method

Examples 1–8 were analyzed by quasielastic light scattering. Specifically, samples for light scattering were filtered with a 0.45 μm filter and analyzed using the Brookhaven Instrument Corporation BI-9000AT autocorrelator and BI-200SM Goniometer. Quasielastic light scattering measurements were performed at an angle of 900 using a laser-derived light source at 488 nm. Measurements were performed at ~0.4 watts. Delay times were set between 0.1 μsec and 150,000 μsec. Samples were equilibrated at 25° C. The analysis was performed using the CONTIN program (Provincher 1982A, 1982B). The analyses indicated that the aqueous pharmaceutical composition contained, inter alia, the 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate) in particle form having a hydrodynamic radius of about 5 to 50 Å.

This indicates that the 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate) is present in monomeric form. In addition, these particles of monomeric form contribute 35%–100% of the total intensity of the linewidth distribution function. This means that about 80 to 100% of the drug by weight is present in particles of monomeric form, in this system. The remaining drug is present in other forms (dimer, trimer, multimer).

What is claimed is:

1. An aqueous pharmaceutical composition comprising an oligosaccharide antibiotic in particles of monomeric form having a hydrodynamic radius of 5 to 50 Å.

2. A composition according to claim 1, wherein said hydrodynamic radius is 7 to 40 Å.

3. A composition according to claim 1, wherein said hydrodynamic radius is 10 to 30 Å.

4. An aqueous pharmaceutical composition comprising on a weight percentage basis:
   a) 0.1 to 10% by weight of an oligosaccharide antibiotic;
   b) 0.001 to 6% by weight, on the basis of said oligosaccharide antibiotic, of a surfactant selected from the group consisting of nonionic, cationic, anionic, or amphoteric, or mixtures thereof;
   c) 0.1 to 10% by weight of a base selected from the group consisting of organic, inorganic, or mixtures thereof;
   d) 1 to 60% by weight of a solubilizing agent selected from the group consisting of a hydroxypropyl α-, β- and γ-cyclodextrins or mixtures thereof.

5. A composition according to claim 4, wherein said surfactant is cationic.

6. A composition according to claim 4, wherein said surfactant is anionic.

7. A composition according to claim 4, wherein said surfactant is amphoteric.

8. An aqueous pharmaceutical composition comprising an oligosaccharide antibiotic in substantially monomeric form wherein 80–100% of the oligosaccharide antibiotic is in particles of monomeric form, wherein further, said particles of monomeric form contribute 35–100% of the total intensity of the linewidth distribution function.

9. An aqueous pharmaceutical composition comprising an oligosaccharide antibiotic in substantially monomeric form wherein 80–100% of the oligosaccharide antibiotic is in particles of monomeric form.

10. An aqueous pharmaceutical composition comprising on a weight percentage basis:
    a) 0.2 to 8.0% by weight of an oligosaccharide antibiotic;
    b) 0.005 to 5% by weight, on the basis of said oligosaccharide antibiotic, of a surfactant selected from the group consisting of nonionic, cationic, anionic, or amphoteric, or mixtures thereof;
    c) 0.3 to 8.0% by weight of a base selected from the group consisting of organic, inorganic, or mixtures thereof;
    d) 2 to 40% by weight of a solubilizing agent selected from the group consisting of a hydroxypropyl α-, β- and γ-cyclodextrins or mixtures thereof.

11. A composition according to claim 10 wherein said oligosaccharide antibiotic is 56-deacetyl-57-demethyl-45-O-de(2-methyl-1-oxopropyl)-12-O-(2,3,6-trideoxy-3-C-methyl-4-O-methyl-3-nitro-α-L-arabino-hexopyransoyl)-flambamycin 56-(2,4-dihydroxy-6-methylbenzoate); said surfactant is selected from polysorbate 80, polyoxyethylene lauryl ether, sodium dodecyl sulfate, cetytrimethylammonium bromide and N,N-bis[3-D-glucoamidopropyl]-cholamide; said base is selected from N-methylglucamine and glycine sodium hydoxide; said solubilizing agent is hydroxyl propyl β-cyclodextrin.

* * * * *